United States Patent

Tappe et al.

[11] Patent Number: 5,856,074
[45] Date of Patent: Jan. 5, 1999

[54] FIXING BATH

[75] Inventors: Gustav Tappe; Norman Klaunzer, both of Leverkusen, Germany

[73] Assignee: Agfa-Gevaert AG, Germany

[21] Appl. No.: 953,262

[22] Filed: Oct. 17, 1997

[30] Foreign Application Priority Data

Oct. 24, 1996 [DE] Germany ................. 196 44 226.5

[51] Int. Cl.$^6$ ...................................... G03C 7/42
[52] U.S. Cl. ................ 430/455; 430/393; 430/400; 430/460
[58] Field of Search .................. 430/455, 491, 430/492

[56] References Cited

U.S. PATENT DOCUMENTS 1,411,687  4/1922  Elliott ................................. 430/455

FOREIGN PATENT DOCUMENTS 446 457  12/1990  European Pat. Off. .
507 145   3/1992  European Pat. Off. .

*Primary Examiner*—Hoa Van Le
*Attorney, Agent, or Firm*—Connolly & Hutz

[57] ABSTRACT

This invention relates to a fixing bath containing a biologically degradable complexing agent of formula I

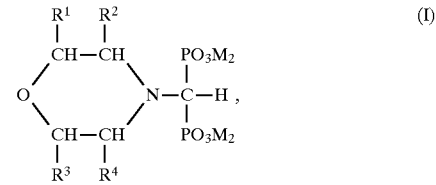

wherein $R^{1-4}$ represents hydrogen, $C_1$–$C_{10}$-alkyl, hydroxy-$C_1$–$C_{10}$-alkyl, $C_1$–$C_{10}$-alkoxy-$C_1$–$C_{10}$-alkyl, carboxy-$C_2$–$C_{10}$-alkyl, dicarboxy-$C_1$–$C_{10}$-alkyl, carboxy-hydroxy-$C_1$–$C_{10}$-alkyl, hydroxy-$C_1$–$C_5$-alkyl-(oxy-$C_1$–$C_5$-alkyl)$_n$, or $C_1$–$C_5$-alkoxy-$C_1$–$C_5$-alkyl-(oxy-$C_1$–$C_5$-alkyl)$_n$, M represents hydrogen, lithium, sodium, potassium or ammonium, and n represents 1, 2, 3 or 4, the iron(III) complex salt of which does not impede electrolytic desilverisation during the regeneration of spent fixing bath.

5 Claims, No Drawings

FIXING BATH

This invention relates to a fixing bath which is suitable for the treatment of photographic silver halide materials and which contains a biologically degradable complexing agent as a lime-preventing agent which masks iron(III) complex salts dragged in by the treatment process. The iron(III) ions thereby lose their oxidising capacity and problems during the electrolytic regeneration of spent fixing bath are avoided.

Sodium or ammonium thiosulphate is predominantly used for fixing. These fixing baths, the pH of which is in the slightly acidic to slightly alkaline range, are usually provided with ethylenediaminetetraacetic acid (EDTA) or nitrilotriacetic acid (NTA) as a lime-preventing agent. Prior art fixing baths are described in U.S. Pat. No. 4,444,873 and EP-A-486 909, for example.

Spent fixing baths contain considerable amounts of dissolved silver. This silver can be recovered, by electrolysis for example. Spent fixing baths are collected for desilverisation; desilverisation in a closed cycle is also possible for modern developing machines which are operated continuously. Corresponding methods are described in J.Appl.Photogr. Engineering 2 (176) 36 and in J. Imaging Techn. 11 (1985) 43.

During the treatment process, iron(III) ions enter the fixing bath due to carry over from the bleaching bath. On account of their pronounced bleaching effect, these iron(III) ions interfere with the electrolytic desilverisation of the spent fixing bath; this can be recognised by the prolonged duration of the electrolysis. Prior art lime-preventing agents are not able to prevent this.

The underlying object of the present invention is to develop a fixing bath which can be used in known treatment processes, and which contains, as a lime-preventing agent, a complexing agent which compensates for the aforementioned disadvantages during electrolytic treatment.

The object is also that the complexing agent should be readily degradable and should give rise to no precipitates in fixing baths which are free from ammonium.

It has now been found that complexing agents of general formula I fulfil the above requirements.

The present invention therefore relates to a fixing bath which contains the necessary active ingredients and auxiliary materials for the fixing process, characterised in that it additionally contains a complexing agent of formula I

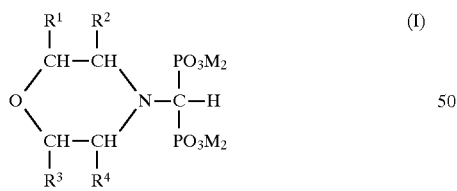

wherein
$R^{1-4}$ represents hydrogen, $C_1$–$C_{10}$-alkyl, hydroxy-$C_1$–$C_{10}$-alkyl, $C_1$–$C_{10}$-alkoxy-$C_1$–$C_{10}$-alkyl, carboxy-$C_2$–$C_{10}$-alkyl, dicarboxy-$C_1$–$C_{10}$-alkyl, carboxy-hydroxy-$C_1$–$C_{10}$-alkyl, hydroxy-$C_1$–$C_5$-alkyl-(oxy-$C_1$–$C_5$-alkyl)$_n$, or $C_1$–$C_5$-alkoxy-$C_1$–$C_5$-alkyl-(oxy-$C_1$–$C_5$-alkyl)$_n$, M represents hydrogen, lithium, sodium, potassium or ammonium, and n represents 1, 2, 3 or 4.

Complexing agents of formula I in which
$R^{1-4}$ represents hydrogen, methyl or hydroxy-$C_1$–$C_{10}$-alkyl, and M represents hydrogen or sodium
are preferably used in the fixing bath according to the invention.

Compounds of formula I which are particularly suitable are given below:

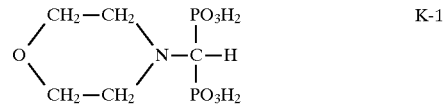

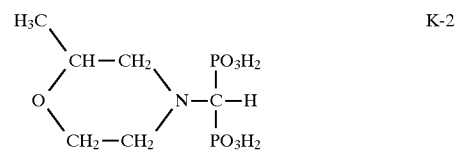

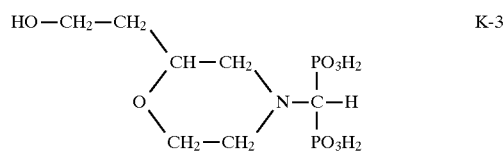

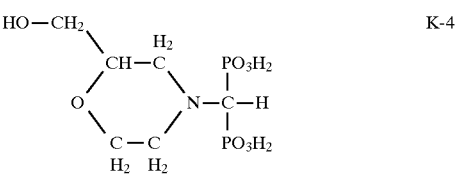

The complexing agents of formula I are usually employed in a concentration of 0.5 to 100 mmol/l, wherein, in a preferred form, the fixing bath according to the invention contains 2 to 30 mmol/l of complexing agent.

Compounds of formula I are known. A method of preparing them is described in DE-A-1 958 123. They have hitherto been used for the softening of water in the cleaning materials sector. EP-A-446 457 and EP-A-507 145 cite them as components of a black and white developer bath for radiography.

The fixing bath according to the invention is particularly suitable for colour photographic silver halide recording materials which contain, on a reflecting or transparent support (e.g. paper coated on both sides with polyethylene or cellulose triacetate film), at least one blue-sensitive, at least one green-sensitive and at least one red-sensitive silver halide emulsion layer, with which there are associated, in the following sequence, at least one yellow coupler, at least one magenta coupler and at least one cyan coupler.

The fixing bath according to the invention is used within the customary treatment process for photographic silver halide materials. Details of the procedure and of the chemicals required therefor are published in Research Disclosure 37 254, Part 10 (1995), page 294 and in Research Disclosure 37 038, Parts XVI to XXIII (1995), page 95 et seq., together with examples of materials.

The treatment process can be conducted continuously, with constant replenishment of the individual treatment baths.

The fixing behaviour of the fixing baths listed in the examples is comparable with a conventional fixing bath containing EDTA.

EXAMPLES

Example 1

A fixing bath of the following composition, which had an accurately defined concentration of calcium ions, was prepared and treated with various complexing agents in different concentrations (Table 1). All the fixing baths according to the invention exhibited no precipitation during the period of observation of 120 days. The fixing baths were stored in open vessels at room temperature. A decrease in volume due to evaporation was compensated for by periodically topping up the baths with deionised water.

| Fixing bath: | |
|---|---|
| water (deionised) | 800 ml |
| sodium sulphate | 10 g |
| sodium sulphite | 20 g |
| sodium thiosulphate | 60 g |
| calcium chloride solution (80 g/l) | 5 ml |
| complexing agent | see Table 1 |

The pH was adjusted to 7 and the baths were made up to 1 liter with deionised water.

TABLE 1

| Experiment No. | Complexing agent | Concentration [mmol/l] | Precipitation |
|---|---|---|---|
| 1 | EDTA | 3.5 | no |
| 2 | PDTA | 3.5 | no |
| 3 | NTA | 3.5 | yes |
| 4 | NTA | 14 | yes |
| 5 | IDA | 3.5 | yes |
| 6 | IDA | 14 | yes |
| 7 | ADA | 3.5 | yes |
| 8 | ADA | 14 | no |
| 9 | ISDA | 3.5 | yes |
| 10 | ISDA | 14 | yes |
| 11 | EDDA | 3.5 | yes |
| 12 | EDDA | 14 | yes |
| 13 | HEDP | 3.5 | yes |
| 14 | HEDP | 14 | yes |
| 15 | MOMP | 3.5 | no |
| 16 | MMOMP | 3.5 | no |
| 17 | HEMOMP | 3.5 | no |

1–14 comparative
15–17 invention
EDTA ethylenediaminetetraacetic acid
PDTA propylenediaminetetraacetic acid
NTA nitrilotriacetic acid
IDA iminodiacetic acid
ADA nitrilodiacetic-monopropionic acid (β-alanine-diacetic acid)
ISDA isoserinediacetic acid
EDDA ethylenediaminediacetic acid
HEDP hydroxyethanediphosphonic acid
MOMP morpholinomethylene-diphosphonic acid
MMOMP 2-methylmorpholinomethylene-diphosphonic acid
HEMOMP 2-hydroxyethylmorpholinomethylene-diphosphonic acid It was only the complexing agents according to the invention which were readily biologically degradable and at the same time, even in low concentration, prevented precipitation.

Example 2

Ammonium-free fixing baths 1 to 8 were prepared in order to illustrate electrolytic regeneration. In order to simulate its spent state, each bath contained a defined amount of silver ions.

| Fixing bath: | |
|---|---|
| water | 800 ml |
| sodium thiosulphate | 35 g |

| Fixing bath: | |
|---|---|
| potassium sulphite | 20 g |
| silver (added as silvere chloride | 2 g |
| ammonium-iron EDTA | see Table 2 |
| complexing agent (see Table 2) | 11 mmol |

The pH was adjusted to 7 and the baths were made up to 1 liter with water.

The electrolysis apparatus contained a curved-round V4A cathode and a rotating graphite anode. The current strength during electrolysis was held constant between 0.2 and 0.22 amperes by an electronic control system. The current density was 5 A/m$^2$. The voltage drifted during the electrolysis—as the silver concentration decreased—from 0.9 to 1.5 volts. The fixing baths were treated using this electrolysis apparatus until the silver content had fallen back to a concentration of 0.5 g/l.

TABLE 2

| Test No. | Ammonium-iron-EDTA | Complexing agent | Duration of electrolysis |
|---|---|---|---|
| 1 | — | EDTA | 3.1 hours |
| 2 | — | MOMP | 3.0 hours |
| 3 | 2 g/l | EDTA | 4.8 hours |
| 4 | 2 g/l | ADA | 5.0 hours |
| 5 | 2 g/l | NTA | 4.9 hours |
| 6 | 2 g/l | MOMP | 3.1 hours |
| 7 | 2 g/l | HEMOMP | 3.2 hours |
| 8 | 2 g/l | MMOMP | 3.2 hours |

1 to 5 comparative
6 to 8 = invention

As can be seen from Table 2, the time of electrolysis is significantly increased when ammonium-iron EDTA is added. The complexing agents which are known from the prior art have no effect on the duration of electrolysis. However, by adding the lime-preventing agents according to the invention the original time of electrolysis as in test 1 (without ammonium-iron EDTA) was obtained again.

The iron was masked by the compounds according to the invention and thereby lost its bleaching capacity and also its negative effect on desilverisation.

The shortened time of electrolysis showed that the current yield was considerably improved by the lime-preventing agents according to the invention.

In addition, ammonium-containing fixing baths 9 to 24 were prepared.

| Fixing bath: | |
|---|---|
| water | 800 ml |
| ammonium thiosulphate | 100 g |
| sodium sulphite | 15 g |
| silver (added as silver chloride) | 2 g |
| ammonium-iron complex | see Table 3 |
| complexing agent (see Table 3) | 11 mmol |

The pH was adjusted to 7 and the baths were made up to 1 liter with water.

Electrolysis was carried out as described above.

TABLE 3a

| Test No. | Ammonium-iron-EDTA | Complexing agent | Duration of electrolysis |
|---|---|---|---|
| 9 | — | PDTA | 3.0 hours |
| 10 | — | HEMOMP | 3.1 hours |
| 11 | 2 g/l | EDTA | 4.8 hours |
| 12 | 2 g/l | PDTA | 4.9 hours |
| 13 | 2 g/l | NTA | 4.9 hours |
| 14 | 2 g/l | MOMP | 3.1 hours |
| 15 | 2 g/l | HEMOMP | 3.1 hours |
| 16 | 2 g/l | MMOMP | 3.2 hours |

9 to 13 = comparative
14 to 16 = invention

TABLE 3b

| Test No. | Ammonium-iron-PDTA | Complexing agent | Duration of electrolysis |
|---|---|---|---|
| 17 | — | NTA | 3.0 hours |
| 18 | — | MMOMP | 3.1 hours |
| 19 | 2 g/l | EDTA | 4.9 hours |
| 20 | 2 g/l | PDTA | 4.8 hours |
| 21 | 2 g/l | NTA | 4.9 hours |
| 22 | 2 g/l | MOMP | 3.0 hours |
| 23 | 2 g/l | HEMOMP | 3.1 hours |
| 24 | 2 g/l | MMOMP | 3.1 hours |

17 to 21 = comparative
22 to 24 = invention

As can be seen from Tables 3a and 3b, a short time of electrolysis, which is comparable with the test without ammonium ions, was also obtained in the presence of ammonium ions. The use of another iron complex (ammonium-iron PDTA instead of ammonium-iron EDTA) also gave the same result.

We claim:

1. A fixing bath which comprises active ingredients and auxiliary materials for the fixing process, and additionally contains a complexing agent of formula I

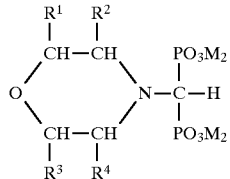

wherein $R^{1-4}$ independently of one another represent hydrogen, $C_1$–$C_{10}$-alkyl, hydroxy-$C_1$–$C_{10}$-alkyl, $C_1$–$C_{10}$-alkoxy-$C_1$–$C_{10}$-alkyl, carboxy-$C_2$–$C_{10}$-alkyl, dicarboxy-$C_1$–$C_{10}$-alkyl, carboxy-hydroxy-$C_1$–$C_{10}$-alkyl, hydroxy-$C_1$–$C_5$-alkyl-(oxy-$C_1$–$C_5$-alkyl)$_n$, or $C_1$–$C_5$-alkoxy-$C_1$–$C_5$-alkyl-(oxy-$C_1$–$C_5$-alkyl)$_n$, M represents hydrogen, lithium, sodium, potassium or ammonium, and n represents 1, 2, 3 or 4.

2. A fixing bath according to claim 1, wherein $R^{1-4}$ represents hydrogen, methyl or hydroxy-$C_1$–$C_{10}$-alkyl, and M represents hydrogen or sodium.

3. A fixing bath according to claim 1, wherein said bath contains an additional complexing agents in a concentration of 0.5 to 100 mmol/l.

4. The fixing bath according to claim 3, wherein the complexing agent of formula I is selected from the group consisting of

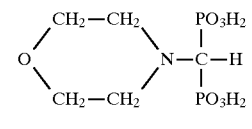

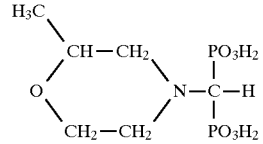

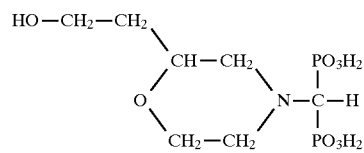

and

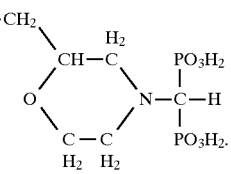

5. The fixing bath according to claim 3, wherein the complexing agents are employed in the concentration from 2 to 30 mmol/l.

* * * * *